United States Patent [19]
Myers

[11] Patent Number: 5,760,237
[45] Date of Patent: Jun. 2, 1998

[54] SYNTHESIS OF L-AZATYROSINE USING PSEUDOEPHEDRINE AS A CHIRAL AUXILIARY

[75] Inventor: Andrew G. Myers, Pasadena, Calif.

[73] Assignee: California Institute of Technology, Pasadena, Calif.

[21] Appl. No.: 519,650

[22] Filed: Aug. 25, 1995

[51] Int. Cl.$^6$ .......................... C07D 213/16; A61K 31/44
[52] U.S. Cl. ........................ 546/300; 514/351; 546/312
[58] Field of Search ................................ 546/312, 300; 504/254; 514/351

[56] References Cited

U.S. PATENT DOCUMENTS

| | | | |
|---|---|---|---|
| 4,618,710 | 10/1986 | Rapoport et al. | 564/1 |
| 4,943,635 | 7/1990 | Corey | 546/548 |
| 5,189,177 | 2/1993 | Blacklock et al. | 548/546 |
| 5,196,607 | 3/1993 | Quallich | 568/327 |
| 5,272,160 | 12/1993 | Chenard | 514/327 |
| 5,286,904 | 2/1994 | Murtiashaw | 562/512 |

FOREIGN PATENT DOCUMENTS 0 430 031 A2  6/1991  European Pat. Off. .

OTHER PUBLICATIONS

Myers, A. G., Yang, B. H., Chen, C. and Gleason, J.L.: Use of Pseudoephedrine as a Practical Chiral Auxilary for Asymmetric Synthesis. J. Am. Chem. Soc. 116:9361–9362, 1994.

Myers, A.G., Yoon, T. and Gleason, J.L.: A One Step Synthesis of Pseudoephedrine Glycinamide, a Versatile Precursor for the Synthesis of α-Amino Acids. Tetrah. Lett. 36:4555–4558, 1995.

Brewsters, R. Q. and McEwen, W.E.: Aliphatic Nitrogen Compounds, in Organic Chemistry, Prentice-Hall, Inc.; 1962; p. 280.

Caine, D., "Alkylations of Enols and Enolates", in Comprehensive Organic Synthesis, Trost, B.M.; Fleming, I., eds.; Pergamon Press: New York, 1991; 1 p.1.

Crosby, D.A., "Synthesis of Optically Active Compounds: A Large Scale Perspective", in Tetrahedron 1991, 47, 4789.

Evans, D., "Stereoselective Alkylation Reactions of Chiral Metal Enolates" in Asymmetric Synthesis, Academic Press, Inc.; 1984; 3, 1.

Larcheveque, M. et al., "Asymmetric Synthesis of α-Substituted Ketones and Acids via Chiral N, N–Substituted Amides" Tetrahedron Lett. 1978, 19, 3961.

Larcheveque et al., "Asymmetric Alkylation of Chiral N, N–Disubstituted Amides", Organomet Chem., 1979, 177, 5.

Evans, D. et al., "Enantioselective Alkylatino of Chiral Enolates", Tetrahedron Lett. 1980, 21, 4233.

Sonnet, P.E. et al., "Asymmetric Alkylation of Amide Anions. Product Analysis by GLC Using Cholesteryl Cinnamate, a Liquid Crystal Phase", J. Org. Chem., 1980, 45, 3137.

Kawanami, Y. et al., "Asymmetric Alkylation of Carboxyamides By Using trans–2, 5–Disubstituted Pyrrolidines as Chiral Auxiliaries", Tetrahedron Lett., 1984, 25, 857.

Enomoto M. et al., "A Highly Effective Asymmetric Synthesis of a α–Hydroxy Acids by Alkylation of Chiral N–(Benzyloxyacetyl)-TRANS-2,5-Bis-(Methoxymethoxymethyl) Pyrrolidine", Tetrahedron Lett., 1985, 26, 1343.

Ikegami, S. et al., "Asymetric Synthesis of α–Amino Acids by Alkylation of a Glycine Amide Derivative Bearing Chiral 2,5–Disubstituted Pyrrolidine as an Amine Component" Tethrahedron Lett., 1986, 27, 3403.

Soai, K. et al., "Asymmetric Synthesis Using Chiral Piperazine. I. Asymmetric Synthesis of 2–Substituted Alcohol and Carboxylic Acid by Diastereoselective Alkylation of Chiral Diamides Derived From Piperazines", Bull. Chem. Soc. Jpn. 1987, 60, 3450.

Ikegami, S. et al., "Asymmetric Synthesis of α–Amino Acids by Alkylation of N[N–Bis(Methylathio) Methylenegylcyl]–2–5 Bis(Methoxymethoxymethyl) Pyrrolidine and Enantioselective Synthesis of Protected (2S, 9S)–2–Amino–8–Oxo–9, 10–Epoxydecanoic Acid", Tetrahedron 1988, 44, 5333.

Juaristi E. et al., "Enantioselective Synthesis of β–Amino Acids. 4. 1,2 Asymmetric Induction in the Alkylation of 1–Benzoyl–3,6(S)–dimethylperhydropyrimidin–4–one. Preparation of the Like and Unlike Stereoisomers of 2–Methyl–and 2–Benzyl–3(S)–aminobutonic Acid" J. Org. Chem. 1993, 58, 2282.

Tamion, R. et al., "Asymmetric Synthesis of New Chiral Auxiliaries Derived From Isosorbide", Tetrahedron: Asymmetry, 1993, 4, 2415.

Schanen, V. et al., "Asymmetric Synthesis. XXXI. Synthesis of 2–Substituted Piperazines From Chiral Non–racemic Lactams", Tetrahedron Lett., 1994, 35, 2533.

Primary Examiner—C. Warren Ivy
Assistant Examiner—Charanjit S. Aulakh
Attorney, Agent, or Firm—Graham & James LLP

[57] ABSTRACT

A practical synthesis of the potential chemotherapeutic agent L-azatyrosine is described. The key step involved the alkylation of (R,R)-(−)-pseudoephedrine glycinamide with 5-benzenesulfonyloxy-2-iodomethylpyridine and proceeded in 70–95% yield and 89–95% de. Simultaneous hydrolysis of the auxiliary and the benzenesulfonate protecting group afforded L-azatyrosine of ≧99% ee in 73% yield on multigram scale (recovery yield of (R,R)-(−)-pseudoephedrine: 90%).

7 Claims, No Drawings

SYNTHESIS OF L-AZATYROSINE USING PSEUDOEPHEDRINE AS A CHIRAL AUXILIARY

This invention relates to chemotherapeutic agents for treatment of neoplastic disease. More particularly, this invention relates to a practical synthesis for the potential chemotherapeutic agent, L-azatyrosine.

BACKGROUND OF THE INVENTION

Oncogenic ras genes and the G-proteins which they encode are important targets for anticancer research. Brunton, V. G., et al., *Cancer Chemother. Pharmacol.* 1993, 32, 1; Prendergast, G. et al., *J. B. Bioessays* 1994, 16, 187. Ras proteins have been implicated as components of the cellular signal transduction pathways related to cell proliferation and differentiation.[1] In their oncogenic form, the natural GTP-ase activity of ras proteins is inhibited, leading to overstimulation of the signaling pathway for cell growth. The potential importance of oncogenic ras genes and gene products as targets for cancer chemotherapy is underscored by the observation that up to 40% of human colon tumors and 95% of human pancreatic tumors have been found to contain oncogenic ras genes. a) Almoguera, et al., *Cell* 1988, 53, 549; Bos, J. L., et al., *Nature* 1987, 327, 293; Forrester, K., et al., *Nature* 1987, 327, 298.

[1] For reviews on ras genes and proteins see: a) Barbacid, M. *Ann. Rev. Biochem.* 1987, 56, 779. b) Prendergast, G. C.; Gibbs, J. B. *Adv. Cancer Res.* 1993, 62, 19.

L-azatyrosine (L-β-(5-hydroxy-2-pyridyl)-alanine)

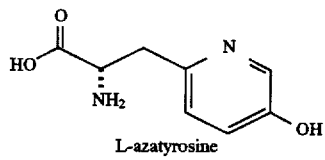

L-azatyrosine is an antibiotic isolated from Streptomyces chibanensis, Inouye, S. et al. T. Chem. Pharm. Bull. 1975, 23, 2669, that has recently been shown to restore normal phenotypic behavior to transformed cells bearing oncogenic ras genes. Shindo-Okada, et al., *Mol. Carcinog.* 1989, 2, 159; Chung, D. L.; et al., *Anticancer Res.* 1991, 11, 1373; Fujita-Yoshigaki, J., et al., *Oncogene* 1992, 7, 2019; Nomura, et al., Jpn. J. Cancer Res. 1992, 83, 851; Campa, M. J. et al, *Proc. Natl. Acad. Sci. U.S.A.* 1992, 89, 7654; Kyprianou et al., J. *Oncogene* 1992, 7, 57. Importantly, L-azatyrosine does not appear to affect cells possessing normal ras genes. Shindo-Okada, et al., *Mol. Carcinog.* 1989, Nomura, et al., Jpn. J. Cancer Res. 1992, 83, 851. In addition, L-azatyrosine has been found to inhibit chemical carcinogen-induced tumor growth in mice harboring normal human c-Ha ras genes. Izawa, M. et al., *Cancer Res.* 1992, 52, 1628.

The limited availability of natural L-azatyrosine for chemotherapeutic studies has stimulated the efforts to synthesize the substance in its optically active form. Schow, S. R. et al., *J. Org. Chem.* 1994, 59, 6850; Ye, B., et al., *J. Org. Chem.* 1995, 60, 2640. Schow et al. employed Williams' method for the asymmetric synthesis of amino acids. Williams, R. M. et al., Tetrahedron Lett. 1988, 29, 6075; Williams, R. M. et al., *J. Am. Chem. Soc.* 1991, 113, 9276. Ye et al. made use of an organometallic coupling protocol using an organozinc reagent derived from iodoalanine. Jackson, R. F. et al., *J. Org. Chem.* 1992, 57, 3397; Dunn, M. J. et al., *Synlett* 1993, 499. The method of Schow et al. requires a relatively expensive chiral auxiliary and employs an unstable bromide intermediate, while the Ye et al. synthesis involves lengthy reagent preparation. Several syntheses of racemic azatyrosine have been published, including a synthesis by Norton et al. that predated the isolation of natural L-azatyrosine by 14 years. Norton, et al., J. Org. Chem. 1961, 26, 1495; Norton, et al., *J. Heterocycl. Chem.* 1970. However, L-azatyrosine is preferred over the racemic mixture because of the biological activity of the L-enantiomer. Inouye, S. et al. T. Chem. Pharm. Bull. 1975, 23, 2669. Accordingly, there is a need for a practical synthesis for L-azatyrosine.

We have recently described a new method for the synthesis of highly enantiomerically enriched α-amino acids that is based on the diastereoselective alkylation of pseudoephedrine glycinamide (2).

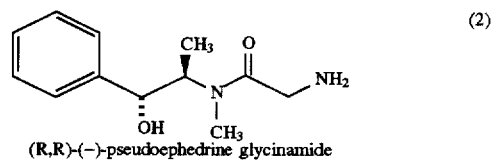

(R,R)-(−)-pseudoephedrine glycinamide

Myers, A. G. et al., *J. Am. Chem. Soc.*, 1995, 117, 8488. See commonly assigned application PCT/US95/03717. The method is well suited to the large-scale preparation of α-amino acids. Both enantiomers of pseudoephedrine glycinamide are readily prepared in large scale in a single step from inexpensive reagents. Myers, A. G. et al., *Tetrahedron Lett.* 1995, 36, 4555. Enolates derived from pseudoephedrine glycinamide are powerful nucleophiles and undergo highly diastereoselective alkylation reactions with a wide range of electrophiles. Importantly, the pseudoephedrine auxiliary is readily removed under mild conditions without significant epimerization of the α-stereocenter. The present invention affords a highly practical preparation of multigram quantities of L-azatyrosine (≧99% ee) using this methodology.

BRIEF SUMMARY OF THE INVENTION

A practical synthesis of the potential chemotherapeutic agent L-azatyrosine is described. The key step involves the alkylation of (R,R)-(−)-pseudoephedrine glycinamide with 5-benzenesulfonyloxy-2-iodomethylpyridine and proceeded in 70–95% yield and 89–95% de. Simultaneous hydrolysis of the auxiliary and the benzenesulfonate protecting group afforded L-azatyrosine of ≧99% ee in 73% yield on multigram scale (recovery yield of (R,R)-(−)-pseudoephedrine: 90%).

DETAILED DESCRIPTION OF THE INVENTION

For the purposes of this invention, the following definitions apply:

Asymmetric Center—an atom in a molecule about which there is no plane of symmetry.

Chiral Auxiliary—an asymmetric molecule which biases a chemical reaction to favor selective formation of one stereoisomer over another.

Chirality—the characteristic of a molecule which cannot be superimposed on its mirror image. A chiral molecule and its mirror image are enantiomers.

Diastereomer—stereoisomers other than enantiomers.

Diastereomeric Excess (de) In a reaction producing only two diastereomers, the excess of the major over the minor divided by the sum of the two. The degree of enrichment is expressed as a percentage.

Enantiomer—one of a pair of isomeric molecules that are non-superimposable mirror images of one another.

Enantiomeric Excess—(ee) the predominance of one enantiomer over the other in a mixture of the two. The degree of enrichment is expressed as the percentage difference of the major enantiomer over the racemate.

Enantiomerically Enriched—when the amount of one enantiomer in a mixture exceeds the amount of the other.

Stereoisomers—Molecules that have the same molecular formula and connectivity, yet differ in the spatial arrangement of their atoms.

The key feature of the synthetic route was the selection of an appropriate 2-halomethyl-5-hydroxypyridine derivative as the electrophilic component in the alkylation reaction. The benzenesulfonyl group proved to be ideal for protection of the phenol group by virtue of its stability to the conditions of free-radical bromination and the conditions of enolate alkylation. In addition, the benzenesulfonyl group conferred greatly enhanced stability to pyridyl benzyl halides such as structures 5 and 6 (versus, e.g., the corresponding silyl ethers employed by Schow et al.) and was readily cleaved under the conditions of auxiliary removal (vide infra). The iodomethyl pyridine derivative (6) is preferred over the bromide (5) because we have generally found alkylations with iodides to be more diastereoselective than the corresponding bromides. Alkylating reagents of this form are useful because of their stability, and may be synthesized using arenes other than benzene, such as para-t-butyl benzene, or other groups that will be apparent to those ordinarily skilled in the art.

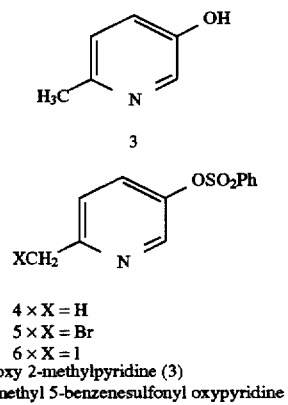

4 x X = H
5 x X = Br
6 x X = I
5-hydroxy 2-methylpyridine (3)
2-halomethyl 5-benzenesulfonyl oxypyridine (5-6)

The iodomethylpyridine derivative 6 was prepared in three steps from commercially available 5-hydroxy-2-methylpyridine. Treatment of 5-hydroxy-2-methylpyridine (1 equiv) with benzenesulfonyl chloride (1.1 equiv) and triethylamine (1.2 equiv) in dichloromethane at 0° C. for 2 h provided the benzenesulfonate derivative 4 in 95% yield. Bromination of the methyl group of the benzenesulfonate derivative 4 was achieved using N-bromosuccinimide (1.4 equiv) with 2,2'-azobis (isobutyronitrile) as initiator in carbon tetrachloride at reflux. The principal by-product of the reaction was the corresponding dibromide, which was readily removed by flash-column chromatography. The desired monobromide (5) was isolated as a white solid (mp 103°–108° C.) in 52% yield. In marked contrast to silyl ether derivatives, brominated benzenesulfonate 5 proved to be stable to storage in the solid state. Finkelstein exchange of the bromide with sodium iodide in acetone produced the crystalline 2-iodomethylpyridine derivative (mp 111°–113° C.) in 93% yield. Like the bromide, the iodide proved to be a storable, stable synthetic intermediate.

The optimum conditions for the alkylation reaction involved the addition of a solution of the 2-iodomethylpyridine derivative (6) (1 equiv) to a solution of the enolate derived from (R,R)-(–)-pseudoephedrine glycinamide (2) [1.5 equiv, generated at 0° C. using 2.93 equiv (relative to 6) lithium diisopropylamide in the presence of lithium chloride (9 equiv) in tetrahydrofuran at –78° C. After 3 h at –78° C., the reaction mixture was warmed to –45° C. and was held at that temperature for 3 h prior to work-up.

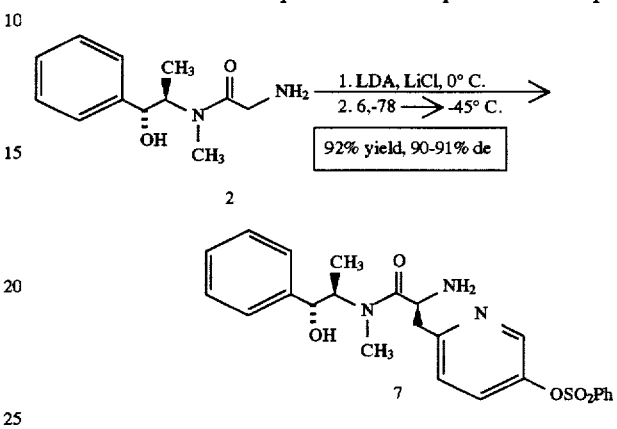

Alklylation Reaction

These conditions typically provided the alkylation product 7 in 90–95% yield after flash column chromatography. It is believed that the product of the alkylation, [R-[R*,R*]-2S*]-N-(2-hydroxy-1-methyl-2-phenylethyl)-N-methyl 2-amino-3-(2-(5-benzenesulfonyloxy)-pyridyl)-propionamide is novel both in racemic mixtures and in enantiomerically enriched form.

A direct method for the analysis of the diastereoselectivity of the alkylation reaction was not found.[2] Therefore, an indirect procedure was adopted involving complete hydrolysis of alkylation product 7 to the amino acid L-azatyrosine (vide infra) followed by analysis of the enantiomeric excess of L-azatyrosine using a chiral HPLC column. Yuki, Y. et al., Chem. Lett. 1986, 1347. In this manner and using the crude alkylation reaction mixture, it was established that the alkylation reaction had proceeded with a minimum diastereoselectivity of 90–91%. When the alkylation reaction was conducted at 0° C., the diastereoselectivity was slightly diminished (89% de), as was the product yield (80%). The maximum reaction diastereoselectivity (94–95% de) was achieved by conducting the alkylation at –78° C.; however, considerable crystallization of the 2-iodomethyl pyridine derivative occurs at this temperature, particularly on larger scales, resulting in diminished yields of product (50–75%). In this context, it is important to note that if complete consumption of the iodide is not achieved, significant N-alkylation of both the starting material, (R,R)-(–)-pseudoephedrine glycinamide and the alkylated product (7) will occur upon concentration after work-up.

[2] ¹H NMR analysis is complicated by the presence of amide rotamers. The involatility of 1 made capillary GC analysis impractical, and conditions for the separation of the diastereomeric alkylation proucts by HPLC have not been found.

The diastereomeric ratio of the alkylation product mixture can be enriched upon flash-column chromatography (4:4:92 methanol:triethylamine: dichloromethane), where the undesired minor diastereomer is found to elute first. In a larger-scale preparation, conducted as in the "optimum" procedure described above and involving purification by flash column chromatography, the alkylation product (7) was obtained in 97% de and 70% yield (25 g). As expected, use of the bromide 5 in the alkylation reaction led to reduced diastereoselectivity (85% de at 0° C.) relative to the iodide.

As in our previous studies, the pseudoephedrine auxiliary was readily cleaved from the alkylation product 7 by basic hydrolysis (4 equiv NaOH, H$_2$O, reflux), conditions which also rapidly hydrolyzed the benzenesulfonate protecting group. Extraction of the crude hydrolysis reaction mixture with dichloromethane led to 90% recovery of the pseudoephedrine auxiliary. Free L-azatyrosine was isolated by ion exchange chromatography (to remove benzenesulfonic acid), followed by recrystallization (H$_2$O). When this procedure was conducted on 7 of 97% de, a 73% yield (7.7 g) of optically pure (≧99% ee) L-azatyrosine was obtained. Hydrolysis of the alkylation product (7) of lower de (90%) also gave reasonable yields of enantiomerically enriched product (47% yield, 99% ee) after a single recrystallization from water. The chemistry described should be readily adaptable to provide enantiomerically pure L-azatyrosine (1) in whatever quantity might be needed.

EXAMPLES

All reagents were commercial materials and were used without further purification with the following exceptions. Tetrahydrofuran was distilled from sodium benzophenone ketyl. Toluene was distilled from calcium hydride. Lithium chloride was dried in vacuo (150° C., 0.5 mm Hg) for 12 h and was briefly flame-dried in vacuo after transfer to reaction flasks. All reactions were carried out under an argon atmosphere. Chromatography was conducted according to the method of Still with 230–400 mesh silica gel. Still, W. C. et al., A. J. Org. Chem. 1978, 43, 2923. NMR spectra were recorded on a GE NMR at 300 MHz for $^1$H and 75 MHz for $^{13}$C. High resolution mass spectra were obtained from the Biomedical Mass Spectrometry Facility, University of California, Los Angeles. HPLC analysis was conducted on a Beckman HPLC equipped with a Chiralpak WH column (available from J. T. Baker Inc.) using, a 0.5 mM CuSO$_4$ mobile phase at 50° C.

Example 1

Synthesis of [R-[R*,R*]]-N-(2-hydroxy-1-methyl-2-phenylethyl)-N-methyl 2-aminoacetamide (R,R)-(−)-pseudoephedrine glycinamide (2)

To a solution of N-tert-butoxycarbonylglycine (20.0 g, 0.114 mol) in CH$_2$Cl$_2$ (400 ml) at 0° C. was added triethylamine (19.1 ml, 0.137 mol, 1.2 eq). To the vigorously stirred reaction mixture was added dropwise trimethyl acetylchloride (14.1 ml, 0.114 mol, 1.0 eq). After 5 min, a fine white precipitate was observed. The reaction was stirred for 45 min at 0° C. and then a second aliquot of triethylamine (19.1 ml, 0.137 mol, 1.2 eq) was added, followed by addition of [R-[R*,R*]]-(−)-pseudoephedrine (18.9 g, 0.114 mol, 1 eq) as a solid. The reaction was stirred for 45 min at 0° C. Most of the solvent was removed in vacuo and the residue was dissolved in MeOH (200 ml) and water (200 ml). The mixture was cooled at 0° C. and treated with c. HCl (150 ml) and vigorous gas evolution was observed. After 2 hr, the methanol was removed in vacuo, and the remaining aqueous was extracted with EtOAc. The organic layer was extracted with 1M HCl. The combined aqueous extracts were cooled to 0° C. and basified to pH 12–14 by slow, careful addition of 50% NaOH. The addition rate was moderated to maintain a solution temperature below 45° C. The aqueous was extracted with CH$_2$Cl$_2$ (4×). The pH of the aqueous after the second extraction was found to be 9 and was readjusted to pH 13 by addition of more 50% NaOH. The combined organic extracts were dried over K$_2$CO$_3$, filtered and concentrated in vacuo. The residue was dissolved in toluene (200 ml) and the solvent removed in vacuo. The oily residue was dissolved in toluene (100 ml), seeded and allowed to stand at 23° C. After the product crystallizes, the recrystallization mixture is cooled to 0° C. for 1 hr before filtration. The filtered crystals were dried in vacuo (0.2 mm) at 55° C. for 12 hr to insure dry product (19.2 g, 76%). Mp. 78°–82° C.; IR (neat) 3361, 2981, 1633, 1486, 1454, 1312, 1126, 1049, 926, 760, 703; $^1$H NMR (1:1 rotamer ratio, CDCl$_3$) 7.29–7.40 (m, 5H), 4.53–4.63 (m, 1.5H), 3.88 (m, 0.5H), 3.72 (d, 0.5H), 3.46 (d, 1H, J=16.6), 3.37 (d, 0.5H, J=17.1), 2.97 (s, 1.5H), 2.79 (s, 1.5H), 2.11 (s(br), 3H), 1.09 (d, 1.5H, J=6.7 ), 0.99 (d, 1.5H, J=6.7); $^{13}$C NMR 174.1, 173.5, 142.3, 142.1, 128.7, 128.5, 127.9, 126.9, 126.7, 75.8, 74.9, 57.5, 57.2, 43.7, 43.4, 30.1, 27.1, 15.3, 14.4; Anal. Calc. for C$_{12}$H$_{18}$N$_2$O$_2$, C, 64.84; H, 8.16; N, 12.60; Found C, 64.54; H, 7.93; N, 12.46.

Example 2

Synthesis of 5-Benzenesulfonyloxy-2-methylpyridine (4)

Benzenesulfonyl chloride (12.9 mL, 101 mmol, 1.10 equiv) was added to a stirred solution of 5-hydroxy-2-methylpyridine (10.0 g, 91.6 mmol, 1 equiv) and triethylamine (15.3 mL, 110 mmol, 1.20 equiv) in dichloromethane (100 mL) at 0° C. After stirring for 2 h at 0° C., water (20 mL) was added and the resulting two-phase mixture was stirred vigorously for 1 h at 23° C. to quench any remaining sulfonyl chloride. Saturated aqueous potassium carbonate solution (100 mL) was added and the layers were separated. The aqueous layer was extracted with a second portion of dichloromethane (150 mL). The combined organic layers were dried over anhydrous potassium carbonate, filtered and concentrated in vacuo. The residue was purified by chromatography on silica gel eluting with a gradient of 4:1 to 1:1 of hexane and ethyl acetate to provide 4 (21.8 g, 95%) as an oil. Chromatography may be avoided by using exactly one equivalent of benzenesulfonyl chloride to afford product of sufficient purity for direct submission to benzylic bromination conditions (see below). IR (neat) 3066, 1594, 1480, 1450, 1384, 1286, 1204, 1177, 1093, 1024, 865, 837, 804, 757, 741, 724, 692; $^1$H NMR (CDCl$_3$) 8.01(d, 1H, J=2.7), 7.84 (d, 2H, J=7.9), 7.70 (t, 1H, J=7.2), 7.55 (t, 2H, J=7.8), 7.33 (dd, 1H, J=8.5, 2.7), 7.13 (d, 1H, J=8.5), 2.53 (s, 3H). Anal. Calcd. for C$_{12}$H$_{11}$NO$_3$S: C, 57.82; H, 4.45; N, 5.62. Found C, 57.66; H, 4.33; N, 5.47.

Example 3

Bromination of 5-Benzenesulfonyloxy-2-methypyridine (4) to yield bromomethylpyridine (5)

A mixture of 4 (33.48 g, 134.3 mmol, 1 equiv) and N-bromosuccinimide (33.47 g, 188.0 mmol, 1.40 equiv) in deoxygenated carbon tetrachloride (300 mL) was heated to reflux. 2,2'-azobis(2-methylpropionitrile) (2.00 g, 11.6 mmol, 0.09 equiv) was added to the refluxing mixture and heating was continued. Additional 2.00-g portions of 2,2$^1$-azobis(2-methylpropionitrile) were added to the refluxing reaction mixture at 30 min intervals over a total reaction period of 2 h. Heating was discontinued after 2 h and the reaction mixture was allowed to cool. The crude reaction mixture was concentrated in vacuo to remove the bulk of the carbon tetrachloride and the resulting slurry was diluted with ethyl acetate (500 mL) and washed with water (400 mL). The organic layer was washed with a mixture of saturated aqueous sodium bicarbonate solution (250 mL) and saturated aqueous sodium thiosulfate solution (100 mL). The aqueous layers were extracted with a second portion of ethyl acetate (250 mL). The combined organic layers were dried over anhydrous sodium sulfate, filtered and concentrated in vacuo. The residue was purified by chromatography on silica gel eluting with a gradient of 4:1 dichloromethane:hexanes to dichloromethane to 10:1 dichloromethane:ethyl acetate to provide 5 (23.08 g, 52%) as a white solid. Mp 103°–108° C.; IR (KBr) 3022, 1584, 1480, 1376, 1368, 1023, 1180, 1087, 1022, 854, 812, 766, 734, 689, 620, 603, 579, 548; $^1$H NMR (CDCl$_3$) 8.12 (s, 1H), 7.86 (d, 2H, J=7.4), 7.72 (t, 1H, J=7.5), 7.57 (t, 2H, J=7.9), 7.45 (d(obs), 2H, J=1.5), 4.51 (s, 2H); $^{13}$C NMR (CDCl$_3$) 155.6, 145.5, 143.4, 134.8, 134.6, 131.0, 129.4, 128.4, 124.2, 32.5. Anal. Calcd. for $C_{12}H_{10}BrNO_3S$: C, 43.92; H, 3.07; N, 4.27. Found C, 43.72; H, 3.01; N, 4.16.

Example 4

Preparation Of 5-Benzenesulfonyloxy-2-iodomethylpyridine (6) By Finklestein Exchange Sodium iodide (5.48 g, 36.6 mmol, 2.00 eqiuv) was added to a solution of 5-benzenesulfonyloxy-2-bromomethylpyridine (6.00 g, 18.3 mmol, 1 equiv) in acetone (75 mL) and the resulting heterogeneous mixture was stirred for 2.5 h at 23° C. Acetone was removed by concentration in vacuo. The residue was diluted with ethyl acetate (100 mL) and the resulting mixture was washed with water (100 ml). The organic layer was extracted with a mixture of saturated aqueous sodium bicarbonate solution (30 mL) and saturated aqueous sodium thiosulfate solution (10 mL). The aqueous layers were extracted with a second portion of ethyl acetate (75 mL). The combined organic layers were dried over anhydrous sodium sulfate, filtered and concentrated in vacuo to produce a yellow-brown solid. The product was recrystallized from a mixture of ethyl acetate (15 mL) and ether (30 mL) to provide 5.18 g of 6 as a stable, light brown crystalline solid. Concentration of the mother liquors and recrystallization provided an additional 1.19 g of 6 (total 6.37 g, 93%). Larger scale preparations of this compound (20 g of 6) provided yields of 75–82%. Mp 111°–113° C.; IR (KBr) 3032, 1584, 1475, 1450, 1375, 1299, 1203, 1179, 1087, 1020, 946, 853, 808, 763, 733, 689, 611, 583, 568, 545; $^1$H NMR (CDCl$_3$) 8.06 (dd, 1H, J=1.0, 2.2), 7.85 (dd, 2H, J=1.0, 8.2), 7.72 (t, 1H, J=6.3) 7.57 (t, 2H, J=7.4), 7.39 (m, 2H), 4.47 (s, 2H); $^{13}$C NMR (CDCl$_3$) 157.1, 144.9, 143.3, 134.7, 134.4, 130.8, 129.4, 128.3, 123.5, 4.5. Anal. Calcd. for $C_{12}H_{10}INO_3S$: C, 38.42; H, 2.69; N, 3.73. Found C, 38.51; H, 2.85; N, 3.47.

Example 5

Diastereoselective Alkylation of (R,R)-(−)-pseudoephedrine glycinamide to yield [R-(R*,R*]-2S*]-N-(2-hydroxy-1-methyl-2-phenylethyl)-N-methyl 2-amino-3-(2-(5-benzenesulfonyloxy)-pyridyl)-propionamide (7)

A solution of n-butyllithium in hexanes (2.64M, 29.5 mL, 78.0 mmol, 2.93 equiv) was added to a solution of diisopropylamine (11.2 mL, 80.0 mmol, 3.00 equiv) in deoxygenated tetrahydrofuran (50 mL) at 0° C. After 15 min, the resulting solution of lithium diisopropylamide was transferred via cannula over 5 min to a stirred slurry of anhydrous R,R-(−)-pseudo-ephedrine glycinamide (8.89 g, 40.0 mmol, 1.50 equiv) and flame-dried lithium chloride (10.2 g, 240 mmol, 9.00 equiv) in deoxygenated tetrahydrofuran (100 mL) at 0° C. After 20 min, the bright yellow suspension was cooled to −78 ° C. and a solution of 6 (10.0 g, 26.7 mmol, 1 equiv) in tetrahydrofuran (40 mL with a 10-mL wash) was added slowly to the reaction mixture. The reaction mixture was stirred for 3 h at −78° C. and was then warmed to −45° C. and stirred for an additional 3 h. Water (400 mL) was added and the resulting two-phase mixture was warmed to 23° C. and extracted with one 400-mL and two 200-mL portions of dichloromethane. The combined organic layers were dried over anhydrous potassium carbonate, filtered and concentrated in vacuo. The residue was purified by chromatography on silica gel eluting with 4:4:92 methanol:triethylamine:dichloromethane. Although the diastereomers were largely separable, they were collected together in order to establish the true overall reaction yield. After concentration of appropriate fractions, the product residue was concentrated from toluene (2×150 mL) and then chloroform (2×150 mL) to remove residual triethylamine. The product (7) was isolated as a very thick oil (11.6 g, 92%). The diastereoselectivity of the reaction was determined by removing a small sample of the crude reaction product (prior to chromatography) and subjecting it to aqueous alkaline hydrolysis conditions (see below), followed by acidification of the aqueous hydrolysis mixture to pH 6 with concentrated phosphoric acid and analysis using a chiral HPLC column (see General Examples). TLC $R_f$ major diasteromer=0.52, minor diasteromer=0.65 (5:5:90 MeOH:NEt$_3$:CH$_2$Cl$_2$). IR (neat) 3352, 3062, 2980, 1634, 1480, 1454, 1379, 1205, 1177, 1093, 1024, 868, 755, 738, 702. $^1$H NMR (approx. 1:1 rotamer ratio, CDCl$_3$) 8.10 (d, 0.5H, J=4.2), 8.09 (d, 0.5H, J=2.7), 7.83 (d, 2H, J=7.2), 7.69 (t, 1H, J=7.4), 7.55 (t, 2H, J=7.9), 7.16–7.41 (m, 7H), 4.71 (d, 0.5H, J=8.4), 4.60 (d, 0.5H, J=9.3), 4.33 (dd, 0.5H, J=6.8, 4.8), 4.16–4.26 (m, 1H), 4.12 (dd, 0.5H, J=7.0, 5.7), 3.44 (dd, 0.5H, J=14.5, 4.7), 3.12 (dd, 0.5H, J=14.5, 7.0), 2.94 (s, 1.5H), 2.90 (s, 1.5H), 2.83–2.99 (m, 1H), 1.5–3.0 (s(br), 3H), 1.01 (d, 1.5H, J=6.9), 0.97 (d, 1.5H, J=6.7); $^{13}$C NMR (CDCl$_3$) 175.3, 174.6, 157.6, 156.9, 144.9, 143.0, 142.8, 142.1, 141.5, 134.9, 134.5, 130.2, 130.1, 129.8, 128.5, 128.3, 128.2, 128.1, 127.6, 127.1, 126.6, 124.8, 124.7, 75.4, 75.3, 59.0, 58.0, 51.6, 51.2, 42.9, 42.7, 32.5, 26.9, 15.7, 14.1. HRMS for $C_{24}H_{28}N_3O_5S$ (MH+) requires 470.1750; Found 470.1737. Anal. Calcd. for $C_{24}H_{27}N_3O_5S$: C, 61.39; H, 5.80; N, 8.95. Found C, 59.96; H, 5.81; N, 8.64.

Example 6

Hydrolytic Cleavage of [R-[R*,R*]-2S*]-N-(2-hydroxy-1-methyl-2-phenylethyl) -N-methyl 2-amino-3-(2-(5-benzenesulfonyloxy)-pyridyl)-propionamide (7) to yield 2-amino-3-(5-hydroxypyridyl)-propanoic acid (L-azatyrosine, (1))

A suspension of 7 (27.22 g, 57.97 mmol, 1 equiv, 97% de) in aqueous sodium hydroxide solution (0.500M, 464 mL, 232 mmol, 4.00 equiv) was heated at reflux for 6 h. The resulting homogeneous solution was then cooled to 23° C. and extracted with two portions of dichloromethane (500 mL, 250 mL). The organic layers were combined and extracted with water (200 mL), then dried over anhydrous potassium carbonate. Concentration of the organic layers provided 8.61 g (90%) of recovered pseudoephedrine. The combined aqueous layers were acidified with aqueous hydrochloric acid solution (1.00M, 232 mL, 232 mmol, 4.00 equiv) producing a slightly acidic solution (pH=3). The volume of the aqueous solution was reduced to approximately 100 mL in vacuo and the concentrate was applied to an ion exchange resin (100 g, Dowex® 50WX4, 50–100 mesh). The resin was flushed with water until the eluent was neutral (pH=6). The product was then eluted with 0.25M aqueous ammonium hydroxide solution (Note: on occasion the product will begin to precipate on the column. In this case, the column contents are transferred to a large sintered-glass funnel and the product is eluted with 0.25M aqueous ammonium hydroxide solution). The ninhydrin-positive fractions were combined and concentrated to provide 9.73 g of a pale yellow solid. The solid was recrystallized from water (400 mL) to afford 4.358 g (41%) of L-azatyrosine as a pale solid. Concentration and crystallization of the mother liquors provided two additional crops of product (3.399 g 32%). If desired, the mother liquors may be decolorized by the addition of activated charcol and filtration through Celite prior to recrystallization. All three crops of amino acid were $\geq$99% ee and all passed CHN analysis. Mp 253°–256° C. decomp., lit[4] 262°–263° C. decomp.; $[\alpha]^{20}_D$=+59.3 (c=1.08, 1N HCl), lit[4]+55 (c=1.1, 1N HCl); IR (KBr) 3084, 2988, 1625, 1597, 1571, 1489, 1410, 1347, 1294, 1255, 1150, 850, 692, 525; $^1$H NMR ($D_2O$) 8.05 (d, 1H, J=2.5), 7.28 (dd, 1H, J=8.5, 2.8), 7.21, (d, 1H, J=8.4), 4.03 (dd, 1H, J=7.9, 5.1), 3.29 (dd, 1H, J=15.1, 5.1), 3.15 (dd, 1H, J=15.1, 7.9). Anal. Calcd. for $C_8H_{10}N_2O_3$: C, 52.74; H, 5.53; N, 15.38. Found C, 52.57; H, 5.65; N, 15.00.

The foregoing examples are intended to be illustrative of the invention, not a limitation thereof. Modifications of the specific examples that are within the scope of the invention will be readily apparent to those skilled in the art. The invention is measured by the claims appended hereto.

I claim:

1. A method for synthesis of L-azatyrosine comprising alkylation of the enolized form of (R,R)-(−)-pseudoephedrine glycinamide, with an appropriate 2-halomethyl-5-hydroxypyridine derivative as the electrophilic component in the alkylation reaction.

2. The method of claim 1 wherein the alkylating agent is 5-benzenesulfonyloxy-2-iodomethylpyridine.

3. The method of claim 1 wherein the alkylating agent is 5-benzenesulfonyloxy-2-bromomethylpyridine.

4. Diastereomerically enriched [R-[R*,R*]-2S*]-N-(2-hydroxy-1-methyl-2-phenylethyl)-N-methyl 2-amino-3-(2-(5-benzenesulfonyloxy)-pyridyl)-propionamide.

5. 2-halomethyl 5-arenesulfonyl oxypyridine.

6. The 2-halomethyl 5-arenesulfonyl oxypyridine of claim 5, wherein the halo atom is selected from the group consisting of iodine and bromine.

7. 2-halomethyl 5-arensulfonyl oxypyridine of claim 5, wherein the arene group is selected from the group consisting of para-t-butyl benzene and benzene.

* * * * *